United States Patent [19]

Szekely

[11] 4,368,850

[45] Jan. 18, 1983

[54] DRY AEROSOL GENERATOR

[76] Inventor: George Szekely, 7 Pamela La., Rochester, N.Y. 14618

[21] Appl. No.: 112,887

[22] Filed: Jan. 17, 1980

[51] Int. Cl.$^3$ .............................................. B05B 9/043
[52] U.S. Cl. ................................ 239/333; 128/200.22
[58] Field of Search ............... 239/333, 338, 334, 329, 239/331, 343, 357, 370, 318, 426; 128/200.22, 200.18; 222/631, 634, 321, 385; 406/38

[56] References Cited

U.S. PATENT DOCUMENTS

| | | | |
|---|---|---|---|
| 3,404,843 | 10/1968 | Szekely | 239/338 |
| 3,522,806 | 8/1970 | Szekely | 239/338 X |
| 3,790,086 | 2/1974 | Masai | 239/426 X |
| 3,838,686 | 10/1974 | Szekely | 239/338 X |
| 4,214,677 | 7/1980 | Bauer et al. | 239/333 X |

Primary Examiner—Robert B. Reeves
Assistant Examiner—Gene A. Church
Attorney, Agent, or Firm—Martin Lukacher

[57] ABSTRACT

A compact aerosol generator which produces, with a fresh air propellant, microscopically small liquid particles known as a dry aerosol particularly adapted for inhalation therapy has a cylindrical housing with a liquid container and a casing containing a baffling system. An air chamber and a manually operated liquid spray pump are defined by telescoping tubes in the housing. Liquid spray ejected from a nozzle at the outlet of the pump enters a jet tube which forms a venturi with a baffle adjacent the nozzle. Passages having their axes perpendicular to the axis of the nozzle provide communication between the air chamber and the jet tube in the vicinity of the outlet of the nozzle. When the telescoping tubes of the pump and air chamber enter each other, pressurized liquid spray and injected air, which is pressurized in this air chamber, flow and combine to efficiently form a spray which is atomized in the baffling system to provide the dry aerosol at the output of the generator. The telescoping tubes are also used for draining the liquid from the generator case to the liquid container. If the device is closed with its cover, the telescoping tubes cover automatically the liquid and air openings of the liquid container to avoid leakage.

13 Claims, 6 Drawing Figures

DRY AEROSOL GENERATOR

The present invention relates to aerosol generators and particularly to manually pumped aerosol generators which can produce a microscopically fine aerosol, with a fresh air propellant.

The invention is especially suitable for use in inhalation therapy and may also find application for cosmetic and hygienic purposes, wherever microscopically small liquid particles are desired.

This invention is an improvement upon the inventions described in the following United States Patents of George Szekely: U.S. Pat. No. 3,302,374 issued Feb. 7, 1967; U.S. Pat. No. 3,404,843 issued Oct. 8, 1968; U.S. Pat. No. 3,522,806 issued Aug. 4, 1970; and U.S. Pat. No. 3,838,686 issued Oct. 1, 1974. Each of these patents is for aerosol apparatus for inhalation therapy which produces a liquid aerosol spray of microscopically fine particles. These sprays are sometimes known as dry aerosols. By a dry aerosol is meant a liquid which is atomized or nebulized to such an extent that the liquid particles do not wet a dry surface. Such sprays have particle sizes less than 10 microns. A fine dry aerosol spray desirably has particles of liquid in the range of 0.5 to 5 microns. Such sprays are especially suitable for inhalation therapy since they are believed not to agglomerate in the alveoli.

The generation of the dry aerosol in a compact, portable device which can easily be handled by the user and which does not require special propellants such as fluorocarbons, presents difficult problems in fluid mechanics. These problems are compounded when the aerosol generators must be capable of being mass produced at low cost.

Accordingly, it is an object of the present invention to provide an improved dry aerosol generator for producing a dry aerosol with a fresh air propellant.

It is a further object of the invention to provide an improved dry aerosol generator which eliminates the need for a propellant other than ambient air and does not require propellants such as compressed air or other compressed gas, and particularly propellants such as fluorocarbons which may constitute a health hazard or which may be prohibited by law or government regulations.

It is a further object of the invention to provide an improved dry aerosol generator of the type in which the flow of liquid under pressure causes, at least in part, the flow of air in the course of atomization of the liquid into the aerosol.

It is a still further object of the invention to provide an improved dry aerosol generator which is compact in size and can be carried in the pocket of the user.

It is a still further object of the invention to provide an improved dry aerosol generator which becomes sealed against leakage of liquid when stowed away and not in use.

It is a still further object of the present invention to provide an improved self-propelled and hand-held dry aerosol generator which is of such shape and size as to occupy essentially a cylinder which, for example, can be approximately 1.5 inches in diameter and three inches long.

It is a still further object of the invention to provide an improved self-propelled, hand-operated dry aerosol generator which is of a construction that eliminates the need for a separate carrying case and may use its own cap as the case.

It is a still further object of the present invention to provide an improved self-pumped dry aerosol generator in which moveable or flexible drain tubes for liquid collected in the atomizing process are eliminated.

It is a still further object of the present invention to provide an improved aerosol generator in which the pressurized liquid does not have to change direction, as from the vertical to the horizontal, in its path from the liquid supply to the spray forming nozzle of the generator and thereby reduces losses in the liquid flow channel and increases efficiency of aerosol production.

It is a still further object of the invention to provide an improved dry aerosol generator where introduction of air is reinforced by the injection of pressurized air coincidentally upon the injection pressured liquid spray, as from a direction perpendicular to the direction of travel of the spray.

It is a still further object of the present invention to provide an improved dry aerosol generator in which pressurized liquid is injected and air which is pressurized is also injected simultaneously with the liquid to enhance the production of the dry aerosol.

It is a still further object of the invention to provide an improved dry aerosol generator which with the same pumping action obtains pressurization of the liquid and pressurization of the air which is injected to enhance the production of the dry aerosol, as when the user pumps the generator to produce a burst of the aerosol.

It is a still further object of the invention to provide an improved dry aerosol generator in which pressurization of the liquid and air pressurization for enhanced jet formation are obtained in a compact structure, as through the use of separate concentric sections having moveable portions in telescoping relationship to pressurize the air and liquid simultaneously.

It is a still further object of the present invention to provide a dry aerosol generator in which the liquid propelling portion of the generator as well as the dry aerosol producing and output portions thereof are in alignment and may be vertically oriented one above the other along a common axis during use.

It is a still further object of the present invention to provide an improved dry aerosol generator having an atomizing baffle which is of such a form as to provide both baffling and venturi action for the propulsion of the liquid particles in the spray and which may be disposed in the immediate vicinity of the nozzle outlet.

It is a still further object of the present invention to provide an improved dry aerosol generator which is adapted to be operated with its baffling system for separation of coarse liquid particles from the fine particles in an axially vertical position to enhance separating action therein.

Briefly described a dry aerosol generator using an ambient, fresh air propellant, embodying the invention, comprises a housing with means for containing a supply of liquid and a nozzle. The nozzle has a spray outlet. Means in the housing defines a chamber for air which is in communication with the vicinity of the nozzle outlet by way of propulsion passages, preferably in a direction perpendicular to the direction of movement of the spray. Means are provided for pumping liquid from the supply through the nozzle simultaneously with the injection of pressurized air from the chamber through the propulsion to provide an aerosol at the outlet of the generator. The pumping means may be in the form of telescoping tubes which define the air chamber and the cylinder in which a liquid pumping piston moves. Baffling means includes a baffle in the immediate vicinity of the nozzle outlet of egg shape as to assist in the separation of the coarse particles from the fine particles and the atomization thereof. This shaped baffle also forms a venturi preferably in vertical alignment with the liquid supply, nozzle and propulsion passages. The baffling means cooperates with the pumping means to produce a dry aerosol spray at the outlet of the generator.

Preferably all of the features of the invention are used together to provide a compact dry aerosol generator which is manually activated with a fresh air propellant. One or more of the features of the invention, such as the simultaneous air and liquid pressurization means, the air introduction passages, and the improved baffling system may be used individually to provide improvements in aerosol generation.

The foregoing and other objects, features and advantages of the invention as well as a presently preferred embodiment thereof will be more apparent from a reading of the following description in connection with the accompanying drawings in which.

Figure 6:
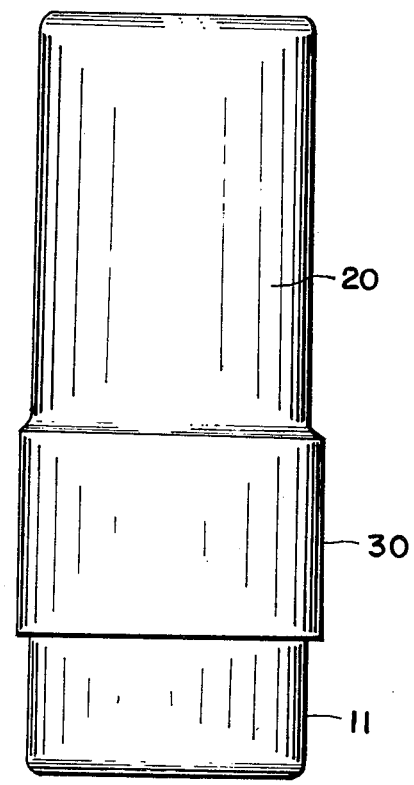
FIG. 6 is a elevational view of the generator shown in FIGS. 1 through 5 with the covering cap in place so that the generator may be stowed away when not in use.

Referring to the drawings, there is shown an aerosol generator 1 which is overall of a cylindrical shape. A housing 30 is provided by a flanged disc 12. The flange is threaded to receive a liquid supply container 11 below, and a closing cover or cap 20 above, the disc 12. The cover is shown unscrewed in FIG. 1 and screwed down into the flanged disc 12 of the housing 30 in FIG. 6. The liquid container 11 is readily refillable by unscrewing it from the lower flange of the disc 12.

The spray forming section of the generator 1 is disposed in the housing above the liquid container 11 and is supported on the disc 12. A nozzle 8 has a skirt 7 which is disposed in telescoping relationship with a manually actuable pump mechanism 9. This pump has a cylinder 13 fixed to the disc 12. The cylinder is closed at its upper end. The bottom end of the cylinder 13 is open and extends below the level of the liquid in the container 11. A tube 16 having a flange is slideably mounted in the cylinder 13. The flange forms a piston 15. An axial hole through the piston extends through the nozzle 8. The spray exits from the nozzle 8 into a region 31 immediately adjacent the output of the nozzle where the spray is produced when the pump 9 is actuated.

Figure 1:
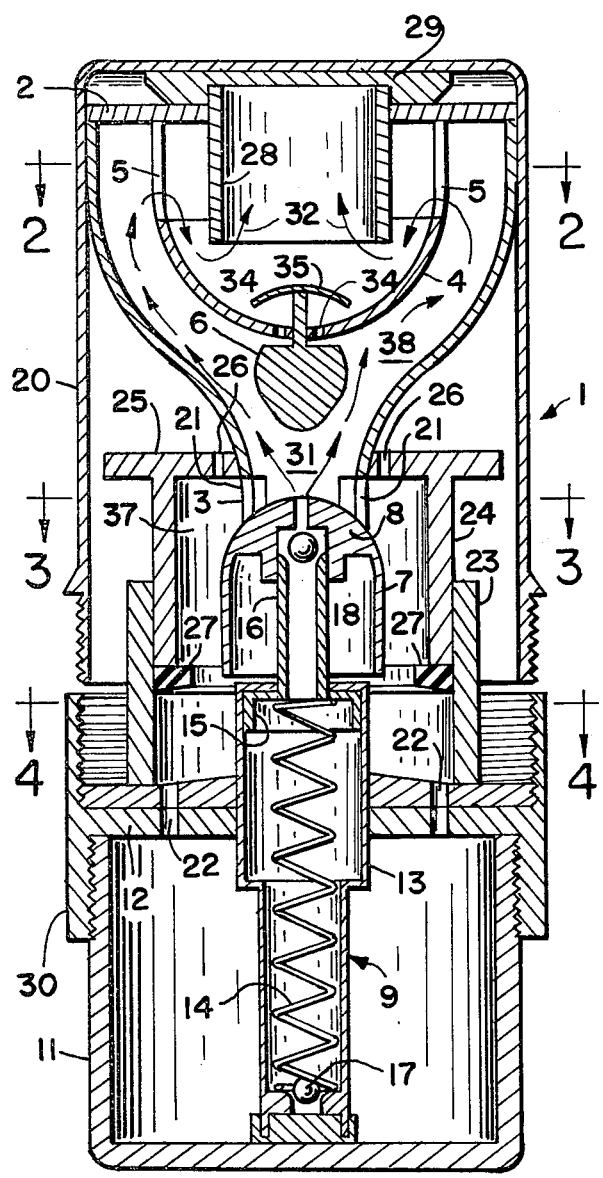
FIG. 1 is a sectional view, in elevation, of a manually-pumped dry aerosol generator embodying the invention.
Figure 2:
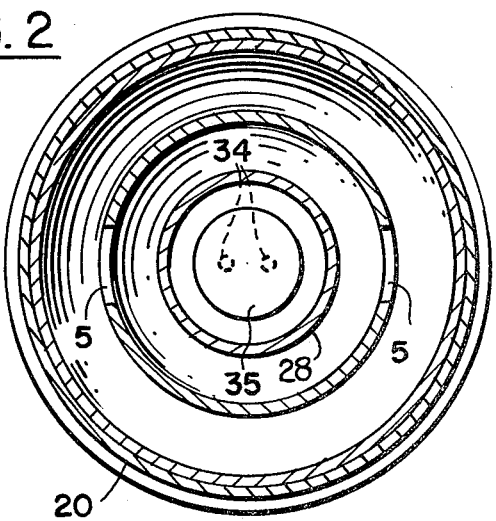
FIGS. 2, 3 and 4 are sectional plan views of the generator shown in FIG. 1, the sections being taken along the lines of 2—2, 3—3, and 4—4 in FIG. 1, respectively.

A spring 14 biases the piston 15 to its upper position as shown in FIG. 1. This spring also retains a lower ball valve 17. An upper ball valve 18 is retained at the upper end of the piston tube 16.

Attached to the nozzle and moveable therewith is a jet tube 3 which provides a propulsion passage and which flares into a casing section. The casing section of the jet tube 3 supports a baffling system. An outlet tube 28, which may be closed by a plug 29, is carried in a disc which provides the upper end 2 of the casing section.

Also attached to the jet tube 3 is a disc 25 which provides a cover for an air chamber 37. This chamber is defined by a cylindrical tube 23 which is supported on the housing disc 12. An inner cylindrical tube 24 is slidably mounted in the outer tube 23. The air chamber 37 is collapsible when the chamber cover 25 and the outer tube 24 is telescoped into the inner tube 23. The skirt 7 of the nozzle 8 also telescopes over the cylinder 13. The piston 15, which is fixed to the nozzle 8 moves vertically downward into the cylinder. The top of the cover 25 and the bottom of the container 11 may be grasped between the fingers and thumb such that the entire upper section of the generator 1 moves downwardly with respect to the lower section in the direction shown by the arrows 38 in FIG. 5.

Liquid which has entered the cylinder 13 through the lower ball valve 17 is pumped upwardly through the piston 15 and the piston tube 16. The upper ball valve moves out of the way in response to the pressurized flow of the liquid and a spray is ejected in a cone-shaped spray through the nozzle 8 into the region 31 in the vicinity of the outlet thereof.

Figure 3:
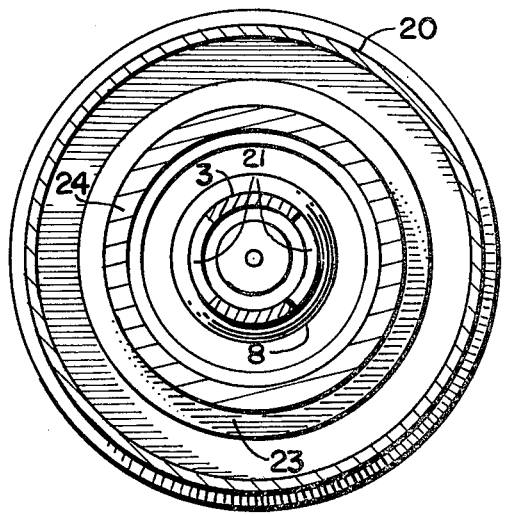
Figure 4:
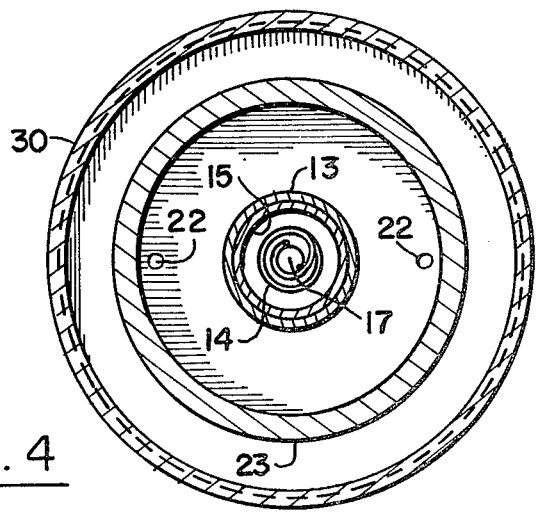

Horizontal passages formed by the air slots 21 in the jet tube 3 provide communication between the air chamber 37 and the region 31 at the outlet of the nozzle. The axes of these slots 21 is transverse, and preferably perpendicular, to the direction of movement of the spray. Two slots 21 are shown on FIG. 3. Other arrangements, such as four slots 21 ninety degrees apart may alternatively be used. The movement of the spray is along the axis of the generator and axis of the openings 21 is perpendicular to the axis of the generator. The axis of the slots 21 intersects the axis of the generator at the outlet of the nozzle 8; that is at the convex extremity or tip of the nozzle 8 which is at the upper end thereof as shown in FIG. 1. Air, which is entrained with the liquid spray in the propulsion passage of the jet tube to form the aerosol, moves through these openings 21 into the jet tube 3 where the aerosol forming action occurs. The air, which is used, is ambient fresh air. Special pressurized propellants, either fluorocarbons, pressurized containers of gas or air or separate motorized pumps are not required in the operation of the generator.

The air enters the chamber 37 through small holes 26 which are much smaller in diameter than the holes 21. When the chamber 37 is collapsed, the air in the chamber 37 is pressurized. Such pressurization occurs simultaneously with the pressurization of the liquid in the cylinder 13 of the pump 9. Both pressurized air and pressurized liquid are produced at the same time. The liquid forms the spray in the region 31 and the pressurized air is injected through the slots 21 to reinforce and enhance the aerosol propulsion and formation in the jet tube 3.

The efficiency of operation is enhanced by virtue of the liquid passages being in line along the vertical axis of the generator. No changes in direction which can cause either turbulant or resistive losses in the liquid path are existent in the generator. Moreover, the horizontal openings 21 for the injection of fresh air in the horizontal direction to the vertically upward moving liquid spray enhances and reinforces the jet action in forming the microscopic aerosol. The jet action is further reinforced by reason of the pressurized air simultaneously and automatically obtained when the liquid is pumped and with the same manual action as is used to pump the liquid.

The baffling system of the generator 1 provides additional advantages of simplicity of construction. A baffle 4 having a hemispherical lower section and an upper section which is open except for support tabs 5 is connected by these tabs 5 to the case section cover 2. A special egg-shaped baffle 6 is attached by a rod to the hemispherical baffle 4. The axis of this baffle 6 is along the vertical axis of the generator. The end of the baffle 6 which faces the outlet of the nozzle 8 and defines the region 31 is hemispherical in shape. The baffle 6 flares outwardly from this hemispheric lower section thereof and defines a tubular channel 38 of reduced diameter with the outwardly flaring walls of the jet tube. This channel 38 is directly in communication with the region 31 at the outlet of the jet tube 3 and provides the only venturi in the baffling system. Because of the shape and location of the baffle 6, multiple venturies which require additional parts are eliminated.

The cone of spray from the nozzle 8 consists of fine particles along its outer periphery and coarser particles at the center thereof. These particles are atomized by interaction with the walls of the jet tube and the baffles 4 and 6. The baffle 4 assists the atomizing and the mixing process of the fine liquid particles with the air stream. In contradistinction of the previous devices, the baffle 4 is in the horizontal direction and consequently this permits only the finest liquid particles to reach the inside space 33 of the baffle 4. The atomized spray reinforced by the injected air stream (i.e. the aerosol) passes along the path in the direction of the arrows 32 through the outlet tube 28. The path 32 is a serpentine path. The length of the path may be varied by changing the position of the outlet tube. By axially shifting the output tube 28 in the generator case 1 the fineness as well as the quantity of the dry aerosol output can be adjusted. The coarser particles in this spray are removed by differential action. These particles coalesce on the inner wall of the hemispherical baffle 4 and on a cover 35 for drain openings 34. The particles drain through the passages 34 and back down into the liquid container through passages 22. When the cover 20 is screwed into the upper flange of the housing 30, seals 27 move into a position to close the drain openings 22 and seal the liquid in the housing. The screwed on cover 20 also insures that no liquid will leak from the generator.

Figure 5:
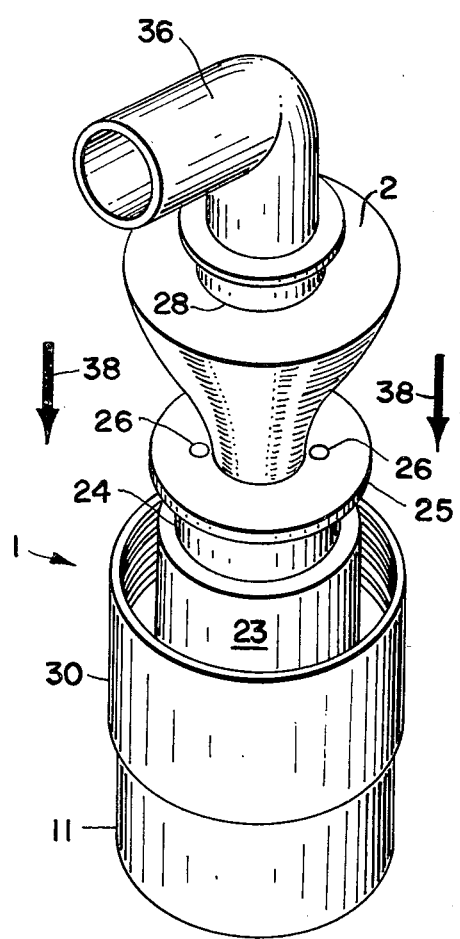
FIG. 5 is a perspective view of the generator shown in FIGS. 1 through 4 with the covering cap thereof removed and with a diverting tube installed at the output of the generator.

The generator may be used in the vertical position as shown. The outlet tube is then inserted into the mouth of the user. Complementary air to assist breathing enters exclusively through the generator insuring that only the medicated aerosol is inhaled. If a bending of the users neck is not possible, a diverting tube 36 may be inserted into the outlet tube 28 as shown in FIG. 5.

From the foregoing description it will be apparent that there has been provided an improved aerosol generator which is especially adapted to generate a dry aerosol. Variations and modifications of the herein described generator, within the scope of the invention, will undoubtedly suggest themselves to those skilled in the art. The foregoing description should therefore be taken as illustrative and not in a limiting sense.

I claim:

1. An aerosol generator comprising a housing, means for containing a supply of liquid in said housing, a nozzle in said housing, said nozzle having a spray outlet, means in said housing defining a chamber for air, a propulsion passage in the vicinity of the nozzle, outlet means providing communication between said chamber and said propulsion passage, and means for simultaneously pumping pressurized liquid from said containing means through said nozzle and injecting pressurized air from said chamber into said propulsion passage to combine in said propulsion passage in the formation of an aerosol, said simultaneous pumping means comprising means forming pistons facing the air in said chamber and the liquid in said containing means, said pistons being interconnected for simultaneous relative movement with respect to said air chamber and liquid containing means, said air chamber means comprising a first pair of tubes in telescoping relationship, a cover for said chamber on one of said tubes providing said air chamber piston, a second pair of tubes in telescoping relationship, one of said second tubes being disposed in said liquid containing means for receiving the liquid therein, the other of said second pair of tubes being fixedly connected to said nozzle, said liquid piston being disposed in and moveable with one of said second pair of tubes, and said cover and nozzle being fixedly connected for conjoint movement.

2. The invention as set forth in claim 1 wherein said first pair of tubes are coaxial with said second pair of tubes, and said second pair of tubes are disposed inside said first pair of tubes.

3. The invention as set forth in claim 1 wherein the one of said second pair tubes which is attached to said nozzle has a flared end having a rim disposed in sliding fit relationship with the other of said second pair of tubes, said other second pair tube being attached to said housing and extending into said liquid containing means to receive the liquid therein, said flared end providing said liquid piston, a channel through said second pair tube attached to said nozzle for the passage of liquid into said nozzle.

4. The invention as set forth in claim 3 wherein said nozzle has a tubular skirt disposed in telescoping relationship with the exterior of said other second pair tube for aligning said nozzle as it moves relative to said other second pair tube.

5. The invention as set forth in claim 1 wherein said propulsion passage comprises a jet tube extending outward from said nozzle in the direction of liquid flow therethrough, said jet tube defining a wall of said air chamber, and an opening in said tube adjacent to said nozzle outlet for the flow of air from said chamber in a direction transverse to the direction of liquid flow through said nozzle.

6. The invention as set forth in claim 5 further comprising openings much smaller in diameter than said jet tube openings for the passage of ambient air into said air chamber.

7. The invention as set forth in claim 5 wherein said jet tube is connected to said cover and flares outwardly to define a casing section, baffling means contained in said jet tube casing section defining a channel in communication with said propulsion passage for the aerosol, said channel having a venturi immediately adjacent to said nozzle outlet, and being operative to assist in propelling the finer liquid particles in said aerosol towards the outlet of the generator.

8. The invention as set forth in claim 7 wherein said liquid chamber is disposed at the lower end of said housing, said jet tube, said casing section and said baffling means being disposed at the upper end of said housing, a wall between said upper and lower housing ends which is horizontal when said generator is held vertically during use, openings in said wall for the return of liquid coalesced on said jet tube and baffles which passes through said air opening in the vicinity of said nozzle outlet and through said air chamber.

9. The invention as set forth in claim 8 comprising sealing means carried on the one of said first telescoping tubes which is connected to said cover for closing said drain openings.

10. The invention as set forth in claim 8 comprising a cup-shaped tubular cover member having an open end, fastening means for attaching said tubular cover member at its open end to said housing above said liquid containing means therein with said jet tube baffles and outlet from said generator within the confines of said tubular cover member.

11. A dry aerosol generator which comprises a nozzle, means for injecting a flow of pressurized liquid into said nozzle, a jet tube adjacent to said nozzle, air receiving passages in said jet tube in the vicinity of said nozzle for forming an aerosol with the liquid spray from said nozzle, said jet tube flaring outwardly away from said nozzle, an outlet tube disposed in the end of said jet tube opposite to said nozzle, baffling means for atomizing and separating coarse liquid particles from dry aerosol particles which comprises a first baffle member having an egg shaped surface with a hemispherically shaped surface portion facing the exit of said nozzle and spaced therefrom, said first baffle member having another surface portion extending from said hemispherical surface portion and forming a tubular venturi channel for the aerosol propelled from said nozzle and through which said aerosol travels to said outlet tube, said baffling means further comprising a second hollow cup-shaped baffle member carrying said egg shaped baffle member at the closed end thereof and in vertical alignment therewith, said outlet tube being disposed within said cup-shaped baffle member to define a serpentine path for said aerosol from which coarse air particles of liquid drop vertically as said aerosol travels along said serpentine path.

12. The invention as set forth in claim 11 wherein said generator is adapted for use with the axes of said nozzle and baffling means coaxial with each other, said egg shaped baffle member, said second baffle member and said outlet tube being disposed successively one above the other, in the order set forth.

13. The invention as set forth in claim 12 further comprising drain openings in said second baffle member, a cover disposed inside said second baffle member above and spaced from said drain openings, said drain openings providing drainage for liquid from said first and second baffle members and from said jet tube downwardly toward said nozzle.

* * * * *